(12) United States Patent
Yan et al.

(10) Patent No.: US 9,017,834 B2
(45) Date of Patent: Apr. 28, 2015

(54) LUBRICANTS FOR DATA STORAGE

(71) Applicant: Seagate Technology LLC, Cupertino, CA (US)

(72) Inventors: Xiaoping Yan, Wexford, PA (US); Michael Stirniman, Fremont, CA (US); Qian Guo, Fremont, CA (US); Wenhong Liu, San Jose, CA (US)

(73) Assignee: Seagate Technology LLC, Cupertino, CA (US)

( * ) Notice: Subject to any disclaimer, the term of this patent is extended or adjusted under 35 U.S.C. 154(b) by 252 days.

(21) Appl. No.: 13/645,672

(22) Filed: Oct. 5, 2012

(65) Prior Publication Data

US 2014/0099518 A1   Apr. 10, 2014

(51) Int. Cl.
| | |
|---|---|
| *G11B 5/66* | (2006.01) |
| *C07D 251/30* | (2006.01) |
| *C07D 403/14* | (2006.01) |
| *G11B 5/725* | (2006.01) |

(52) U.S. Cl.
CPC ............ *C07D 251/30* (2013.01); *C07D 403/14* (2013.01); *G11B 5/725* (2013.01)

(58) Field of Classification Search
CPC ....................... C10N 2240/204; C10N 2040/18
USPC ................................. 508/582, 269; 428/835.8
See application file for complete search history.

(56) References Cited

U.S. PATENT DOCUMENTS

| | | | | |
|---|---|---|---|---|
| 3,976,603 | A | * | 8/1976 | Caporiccio et al. ........... 528/401 |
| 5,942,598 | A | * | 8/1999 | Iwa et al. ...................... 528/362 |
| 8,149,534 | B2 | | 4/2012 | Yan |
| 2007/0032390 | A1 | * | 2/2007 | Russo et al. ................... 508/257 |
| 2012/0231297 | A1 | * | 9/2012 | Sugiura et al. ................ 428/810 |
| 2012/0251843 | A1 | * | 10/2012 | Yan et al. ...................... 428/800 |
| 2013/0237462 | A1 | * | 9/2013 | Valsecchi et al. ............. 508/257 |

\* cited by examiner

*Primary Examiner* — Holly Rickman
(74) *Attorney, Agent, or Firm* — Mueting, Raasch & Gebhardt

(57) ABSTRACT

Disclosed herein are compounds of formula I:

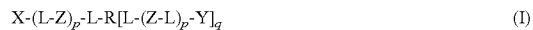

wherein L is a perfluoropolyether;
R is

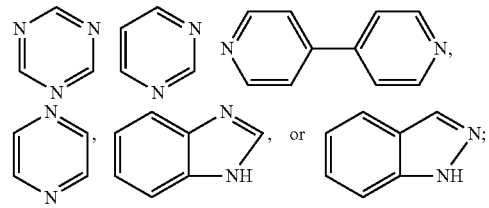

q can be an integer equal to or greater than 1;
p can independently be integers from 0 to 7;
X and Y can independently be chosen from: —OH, —CH$_2$CH$_2$OH, CH$_2$CH$_2$OCH$_2$CH$_2$OH, —CH$_2$CH(OH)CH$_2$OH, —C$_6$H$_5$, —CH$_2$C$_6$H$_5$, —CH$_2$CH(OH)CH$_3$, F, —CF$_3$, —CF$_2$CF$_3$, piperonyl, triazine, benzotriazole, and derivatives thereof; and
Z, if present, can independently be chosen from: —C$_6$H$_4$—, —CH$_2$C$_6$H$_4$CH$_2$—, —CH$_2$CH(OH)CH$_2$—, —CH$_2$CH(OH)CH$_2$CH(OH)CH$_2$—, —CH(OH)CH(OH)CH$_2$—, —CH(CH$_2$OH)—, or —CH(C$_6$H$_5$)—.

2 Claims, 1 Drawing Sheet

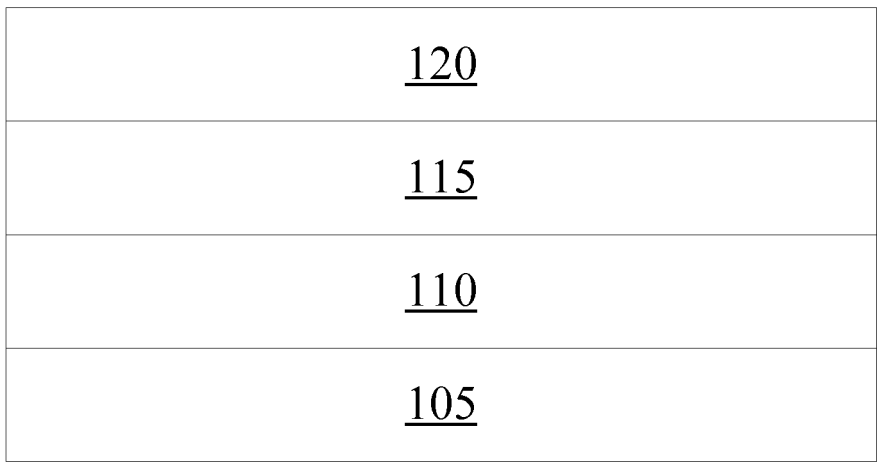

LUBRICANTS FOR DATA STORAGE

BACKGROUND

Magnetic storage media are moved relative to a magnetic head in order to read and write information to and from the magnetic disc. The magnetic storage media, or disc typically includes a substrate, an underlayer, a magnetic layer, an overcoat layer, and a lubricant layer. In order to maximize the capacity of a magnetic disc, the magnetic head desirably flies as close as possible to the magnetic disc. The lubricant layer is designed to reduce the wear that such low flight heights can cause. As the fly height, or head media spacing (referred to as "HMS") decreases, new and more effective lubricants become necessary.

SUMMARY

Disclosed herein are compounds of formula I:

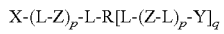   (I)

wherein L is a perfluoropolyether;
R is

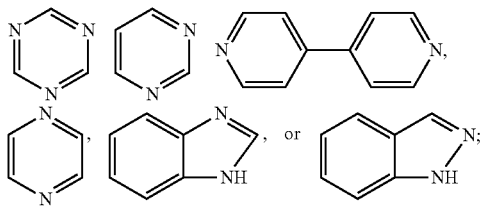

q can be an integer equal to or greater than 1;
p can independently be integers from 0 to 7;
X and Y can independently be chosen from: —OH, —CH$_2$CH$_2$OH, CH$_2$CH$_2$OCH$_2$CH$_2$OH, —CH$_2$CH(OH)CH$_2$OH, —C$_6$H$_5$, —CH$_2$C$_6$H$_5$, —CH$_2$CH(OH)CH$_3$, F, —CF$_3$, —CF$_2$CF$_3$, piperonyl, triazine, benzotriazole, and derivatives thereof; and
Z, if present, can independently be chosen from: —C$_6$H$_4$—, —CH$_2$C$_6$H$_4$CH$_2$—, —CH$_2$CH(OH)CH$_2$—, —CH$_2$CH(OH)CH$_2$CH(OH)CH$_2$—, —CH(OH)CH(OH)CH$_2$—, —CH(CH$_2$OH)—, or —CH(C$_6$H$_5$)—.

Also disclosed herein are magnetic recording media that includes: a substrate, a magnetic layer on the substrate, the magnetic layer configured to store data; a protective overcoat on the magnetic layer; and a lubricant layer on the protective overcoat, the lubricant layer including at least one compound of formula I:

   (I)

wherein L is a perfluoropolyether;
R is

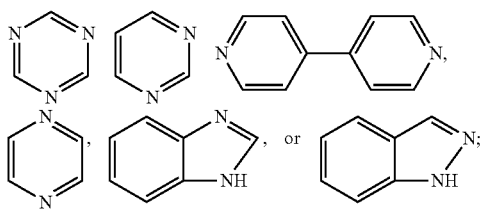

q can be an integer equal to or greater than 1;
p can independently be integers from 0 to 7;
X and Y can independently be chosen from: —OH, —CH$_2$CH$_2$OH, CH$_2$CH$_2$OCH$_2$CH$_2$OH, —CH$_2$CH(OH)CH$_2$OH, —C$_6$H$_5$, —CH$_2$C$_6$H$_5$, —CH$_2$CH(OH)CH$_3$, F, —CF$_3$, —CF$_2$CF$_3$, piperonyl, triazine, benzotriazole, and derivatives thereof; and
Z, if present, can independently be chosen from: —C$_6$H$_4$—, —CH$_2$C$_6$H$_4$CH$_2$—, —CH$_2$CH(OH)CH$_2$—, —CH$_2$CH(OH)CH$_2$CH(OH)CH$_2$—, —CH(OH)CH(OH)CH$_2$—, —CH(CH$_2$OH)—, or —CH(C$_6$H$_5$)—.

Also disclosed herein are magnetic recording media that include a substrate; a magnetic layer on the substrate, the magnetic layer configured to store data; a protective overcoat on the magnetic layer; and a lubricant layer on the protective overcoat, the lubricant layer including at least one compound of formula I:

   (I)

wherein L is —O(CH$_2$)$_c$C$_s$F$_{2s}$O(C$_m$F$_{2m}$O)$_a$(C$_n$F$_{2n}$O)$_b$C$_s$F$_{2s}$(CH$_2$)$_c$O—,
wherein m is an integer from 2 to 5;
n is an integer from 1 to 4;
s is an integer from 1 to 4;
a is an integer from 1 to 1000; and
b is an integer from 0 to 1000;
c is an integer from 0 to 3;
R is

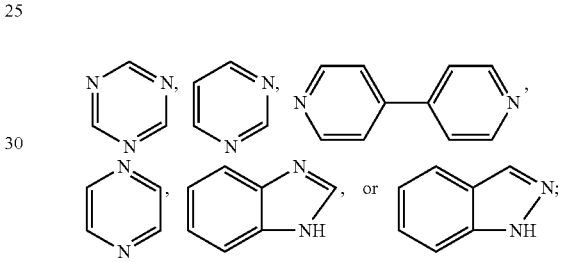

q can be an integer equal to or greater than 1;
p can independently be integers from 0 to 7;
X and Y can independently be chosen from: —OH, —CH$_2$CH$_2$OH, CH$_2$CH$_2$OCH$_2$CH$_2$OH, —CH$_2$CH(OH)CH$_2$OH, —C$_6$H$_5$, —CH$_2$C$_6$H$_5$, —CH$_2$CH(OH)CH$_3$, —F, —CF$_3$, —CF$_2$CF$_3$, piperonyl, triazine, benzotriazole, and derivatives thereof; and
Z, if present, can independently be chosen from: —C$_6$H$_4$—, —CH$_2$C$_6$H$_4$CH$_2$—, —CH$_2$CH(OH)CH$_2$—, —CH$_2$CH(OH)CH$_2$CH(OH)CH$_2$—, —CH(OH)CH(OH)CH$_2$—, —CH(CH$_2$OH)—, or —CH(C$_6$H$_5$)—.

These and various other features and advantages will be apparent from the following detailed description.

BRIEF DESCRIPTION OF THE DRAWINGS

The invention may be more completely understood in consideration of the following detailed description of various embodiments of the invention in connection with the accompanying drawings, in which:

FIG. 1 illustrates a cross section of a magnetic recording media disclosed herein.

The figures are not necessarily to scale. Like numbers used in the figures refer to like components. However, it will be understood that the use of a number to refer to a component in a given FIGURE is not intended to limit the component in another FIGURE labeled with the same number.

DETAILED DESCRIPTION

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

"Include," "including," or like terms means encompassing but not limited to, that is, including and not exclusive. It should be noted that "top" and "bottom" (or other terms like "upper" and "lower") are utilized strictly for relative descriptions and do not imply any overall orientation of the article in which the described element is located.

Disclosed herein are compounds for use as lubricants and magnetic recording media containing such lubricants. Disclosed lubricants can offer corrosion resistant properties, for example. A corrosion resistant lubricant or a lubricant with increased corrosion resistance can ultimately be used in a thinner layer, which could allow for a reduction of the HMS. Disclosed lubricants can include a nitrogen containing moiety as a central group, and can optionally include nitrogen containing groups as end groups. The nitrogen containing group(s) may provide various properties to disclosed lubricants, including, for example: relatively strong bonds to an underlying carbon overcoat which could contribute to the durability of the lubricant; a lower profile lubricant film which could contribute to the reduction in the HMS; relatively high chemical stability, which could contribute to the thermal stability of the lubricant; protection from thermal oxidative or Lewis acid-catalyzed decomposition or some combination thereof.

Exemplary compounds can include compounds of formula I:

X-(L-Z)$_p$-L-R[L-(Z-L)$_p$-Y]$_q$  (I)

In compounds of formula I, L can be a perfluoropolyether. A perfluoropolyeter can be more specifically described as having the formula:

—O(CH$_2$)$_c$C$_s$F$_{2s}$P(C$_m$F$_{2m}$O)$_a$(C$_n$F$_{2n}$O)$_b$C$_s$F$_{2s}$(CH$_2$)$_c$
O— where m is an integer from 1 to 5, n is an integer from 0 to 4, s is an integer from 0 to 4, a is an integer from 1 to 1000, b is an integer from 0 to 1000, and c is an integer from 0 to 3. R can be:

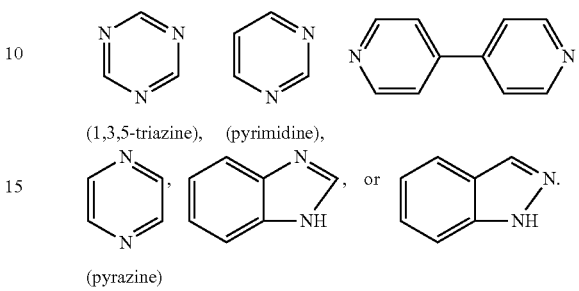

(1,3,5-triazine), (pyrimidine),

, , or .

(pyrazine)

It should be understood that the moiety, "R", can be attached to the opposing "L" moieties at any position within the R moiety. In some embodiments, the moiety, R, can be attached to the opposing L moieties via a carbon atom.

q can be an integer equal to or greater than 1. In embodiments where q is 1, the structure will be linear. In embodiments where q is 2 or greater, the structure will be star- or wheel-like. p can independently be integers from 0 to 7. X and Y can independently be chosen from the following: —OH, —CH$_2$CH$_2$OH, —CH$_2$CH$_2$OCH$_2$CH$_2$OH, —CH$_2$CH(OH)CH$_2$OH, —C$_6$H$_5$, —CH$_2$C$_6$H$_5$, —CH$_2$CH(OH)CH$_3$, —F, —CF$_3$, —CF$_2$CF$_3$, piperonyl, triazine, benzotriazole, and derivatives thereof. Z, if present, can independently be chosen from: —C$_6$H$_4$—, —CH$_2$C$_6$H$_4$CH$_2$—, —CH$_2$CH(OH)CH$_2$—, —CH$_2$CH(OH)CH$_2$CH(OH)CH$_2$—, —CH(OH)CH(OH)CH$_2$—, —CH(CH$_2$OH)—, or —CH(C$_6$H$_5$)—.

In some embodiments, R can be 1,3,5-triazine (C$_3$N$_3$). In some embodiments, L can be polyperfluoropropylene oxide (—OCH$_2$CF$_2$CF$_2$O(CF$_2$CF$_2$CF$_2$O)$_m$CF$_2$CF$_2$CH$_2$O—, commercially available as DEMNUM® from Daikin Fluorochemicals Co., Ltd. (China) and polyperfluoroethylene oxide (OCH$_2$CF$_2$O(CF$_2$CF$_2$O)$_m$(CF$_2$O)$_n$—CF$_2$CH$_2$O, commercially available as FOMBLIN® Z from Solvay Solexis, Inc., West Deptford, N.J.). In some embodiments, X and Y can independently be chosen from —OH, 1,3,5-triazine (C$_3$N$_3$) or derviatives thereof, and benzotriazole or derivatives thereof. In some embodiments, Z can be independently chosen from —CH$_2$CH(OH)CH$_2$— and —CH$_2$C$_6$H$_4$CH$_2$—. In some embodiments, m and n are both independently greater than or equal to 3. Compounds having m and n greater than or equal to 3 can be more resistant to thermal oxidative and/or Lewis acid-catalyzed decomposition. In some embodiments, the number average molecular weight of disclosed compounds can range from 2000 to 4000 g/mol. In some embodiments, the number average molecular weight of disclosed compounds can range from 2500 to about 3500 g/mol.

Specific exemplary compounds that can be utilized can include those below:

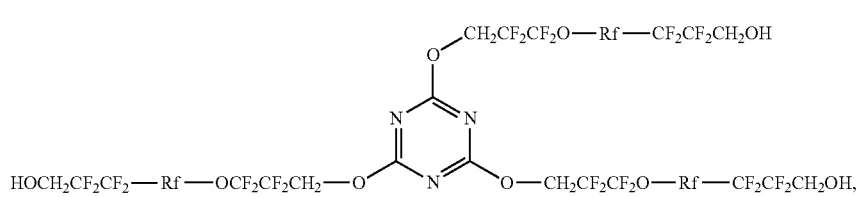

(II)

-continued

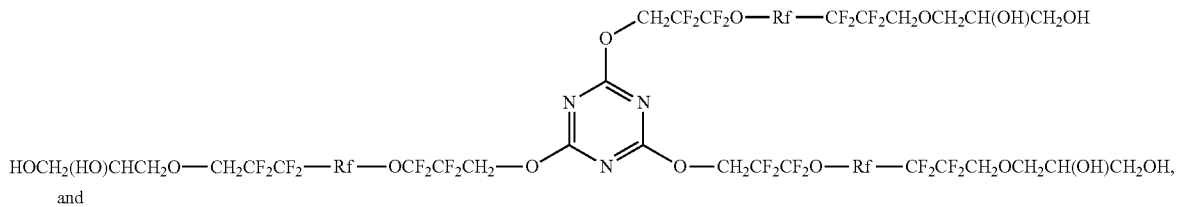

(III)

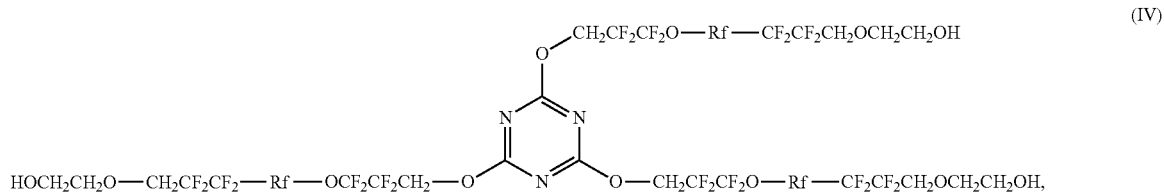

(IV)

wherein $R_f$ is $(CF_2CF_2CF_2O)_m$, where m is an integer greater than or equal to 3.

Additional specific exemplary compounds that can be utilized can include those below:

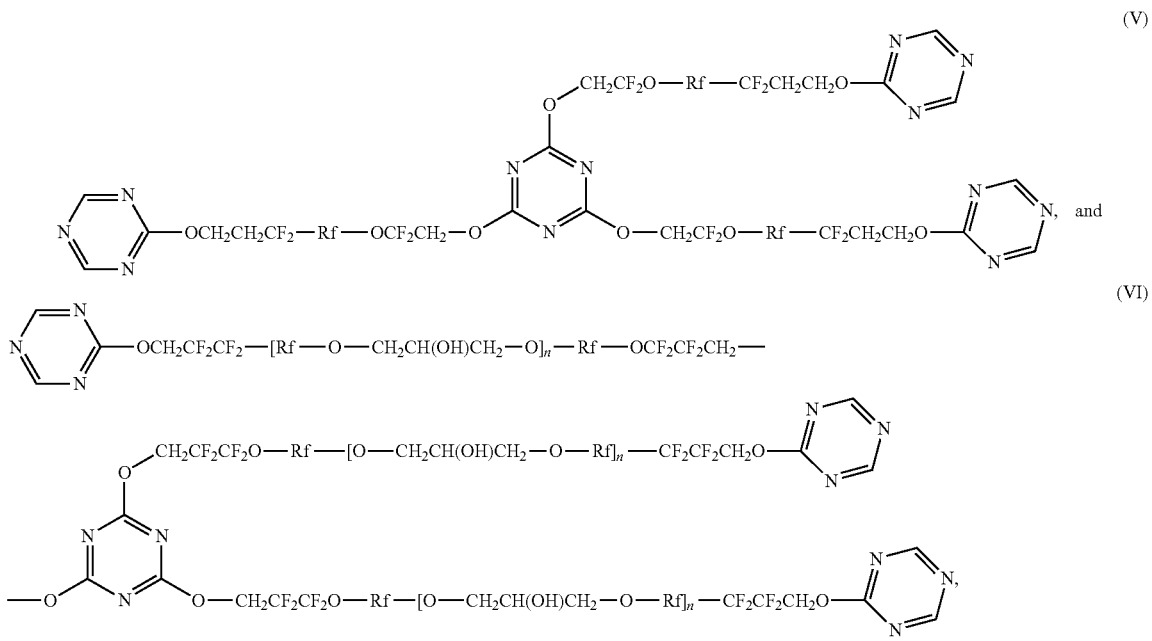

(V)

(VI)

wherein $R_f$ is $(CF_2CF_2CF_2O)_m$, where m is an integer greater than or equal to 3; and n is an integer.

Another specific exemplary compound that can be utilized can include:

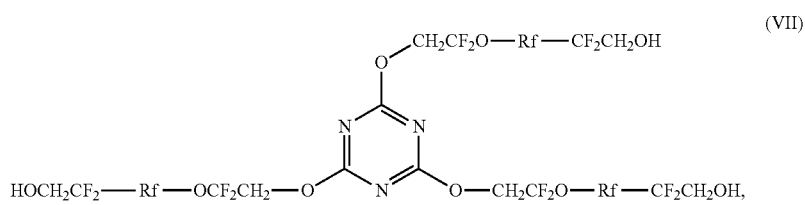

(VII)

wherein $R_f$ is $(CF_2CF_2O)_m(CF_2O)_n$, and m/n is about 1.

Generally, compounds disclosed herein can be synthesized by reacting a N-containing cyclo-chemical that contains the R entity of interest (for example, triazine or its derivatives) and a mixture or single type of perfluoropolyether. This can then be followed by additional processes to purify the yielded compound.

As an example of the disclosure, a compound of formula VII was synthesized and evaluated. The compound having formula VII can be obtained by the following synthesis method. 25 g of 2,4,5-trichloro-1,3,5-triazine (cyanuric chloride) was dissolved in a mixed solvent of trifluoromethylbenzene and 2,4,6-trimethylpyridine. Then 500 g of a perfluoropolyether (FOMBLIN® Zdol, ~1000 in Mn) with one hydroxyl group at both ends was added to the solution. The reaction mixture was agitated for about 25 hours. The resulting mixture was first washed with water followed by subsequent purification by means of column chromatography, yielding ~50 g of the desired Compound VII.

The compound (Compound VII in this example) was coated by dipping the disk into a lube solution in vertrel solvent under controlled lube concentration and pulling out speed or draining speed to achieve the thicknesses indicated in Table 1. For the sake of comparison, FOMBLIN® Z-TETRAOL® 2000 (Solvay Solexis, Inc., West Deptford, N.J.) was also coated in the same fashion. The corrosion resistance of the two compounds was evaluated using transition metal ion chromatography (TMIC) to monitor the amount of cobalt ions. The disks were exposed to a controlled environmental chamber at 130° C. and 95% relative humidity for 10 hours. The disc was then immersed in a HCl/DI water solution at a pH of 3.85 for 1 hour to extract corrosive ions. The surface contamination test was conducted by measuring organic uptake on the disc surface with GC-MS. In this experiment, dioctyl phthalate (DOP) and dioctyl sebacate (DOS) are used as representative organic contaminants from the environment to mimic surface contamination. The disc was kept in a chamber at 50° C. for 2 hrs in the presence of certain amounts of dioctyl phthalate (DOP) and dioctyl sebacate (DOS), then it was kept in the chamber for an additional 9 hrs under ambient conditions. Specifically, the content of total organic contamination TOC) and dioctyle phthalate (DOP) were measured. The results from these analyses can be seen in Table 1 below.

TABLE 1

| Sample | Mw | Thickness | TMIC ($Co^{2+}$) ng/disk | Organic Uptake (ng/surface) TOC | DOP |
|---|---|---|---|---|---|
| Z-TETRAOL | 2700 | 12.6 Å | 58 | 349 | 202 |
| Cmpd. VII | 3200 | 12.3 Å | 13 | 116 | 37 |

As can be seen from Table 1, compound VII performed better than Z-TETRAOL in both corrosion resistance and contamination resistance.

Compounds disclosed herein can be utilized as lubricants or in lubricant compositions. When utilized as a portion of a lubricant composition, other components may be combined with the compound (or compounds) of formula I. Such lubricants can be utilized in magnetic recording media. FIG. 1 depicts a cross section of an exemplary magnetic recording media. The exemplary magnetic recording media or disc 100 can include a substrate 105; a magnetic layer 110 on the substrate, the magnetic layer configured to store data (generally in the form of "0" or "1"); a protective overcoat 115 on the magnetic layer; and a lubricant layer 120 on the protective overcoat. Discs can also include other layers not depicted herein, such as for example underlayers, adhesion layers, etc. Discs, as disclosed herein can be textured or can include various portions, such as a data zone (the portion of the disc configured to store information) and a landing zone (the portion of the disc where the slider that holds the read/write head rests while the disc is not in use and takes off from when the disc drive is started up). Lubricants as disclosed herein can be utilized differently or the same in various portions of discs.

Disclosed compounds or lubricant compositions containing disclosed compounds can be deposited by various means, including for example dip coating, spin-on coating, vapor deposition and/or electrospray.

Compounds disclosed herein can be utilized in the lubricant layer 120. The lubricant layer 120 can function to minimize, reduce or eliminate wear, friction, and stiction between the disc and the read/write head as the read/write head passes over the disc. Generally, the lubricant layer can have a thickness from 3 Å to 30 Å, from 5 Å to 20 Å, or from 8 Å to 15 Å. The lubricant layer can be either partially bonded to the underlying carbon overcoat or fully bonded.

Compounds disclosed herein can provide various properties as lubricants or in lubricant compositions.

Thus, embodiments of lubricants for data storage are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. A compound selected from the following compounds:

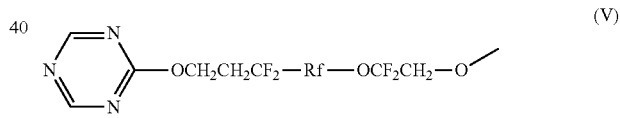

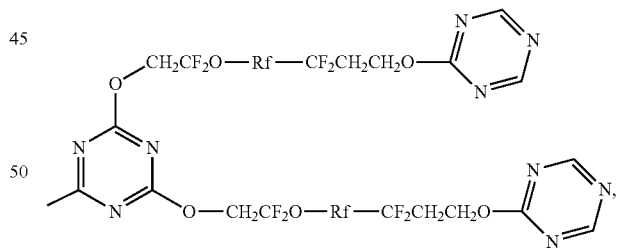

or

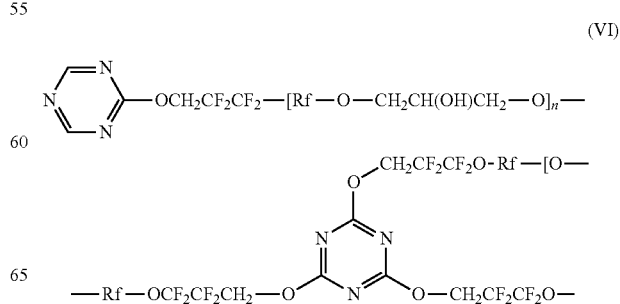

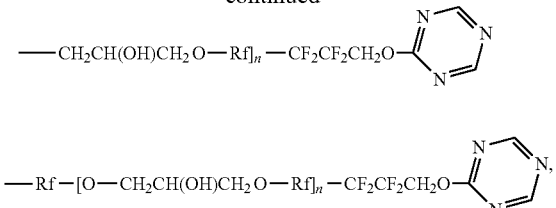

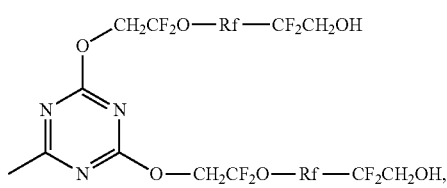

wherein $R_f$ is $(CF_2CF_2CF_2O)_m$, where n is an integer greater than or equal to 3, and m is an integer; or wherein $R_f$ is $(CF_2CF_2O)_m(CF_2O)_n$, and m/n is about 1.

2. A magnetic recording medium comprising:
a substrate;
a magnetic layer on the substrate, the magnetic layer configured to store data;
a protective overcoat on the magnetic layer; and
a lubricant layer on the protective overcoat, the lubricant layer comprising at least one compound (VII)

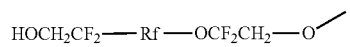

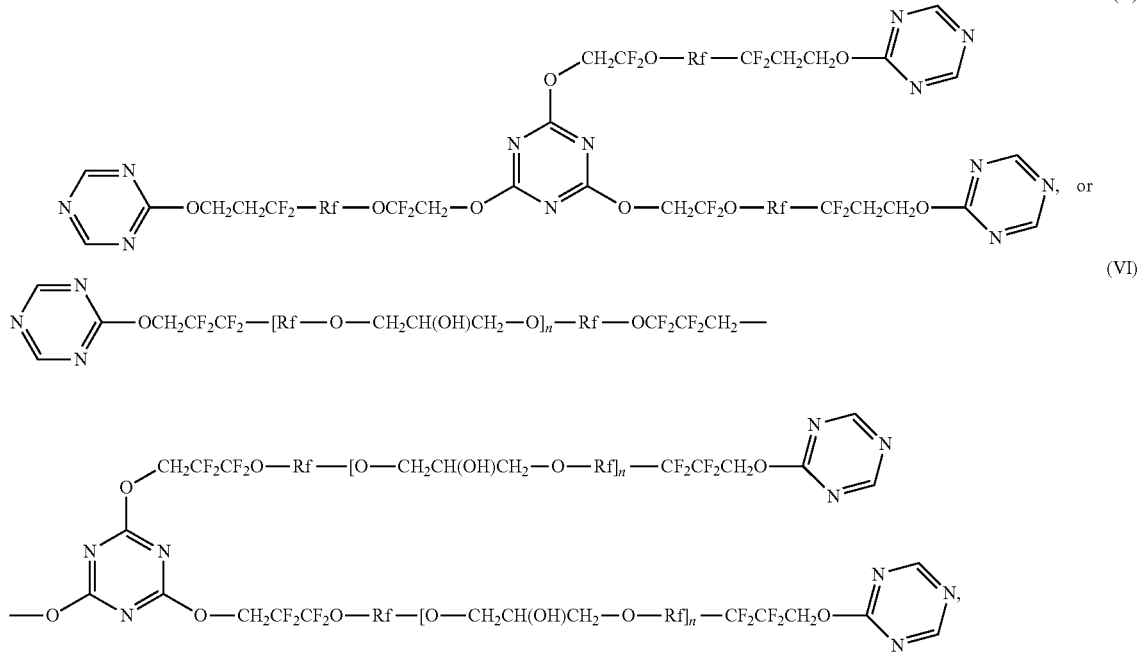

wherein $R_f$ is $(CF_2CF_2CF_2O)_m$, where n is an integer greater than or equal to 3, and m is an integer; or (VII)

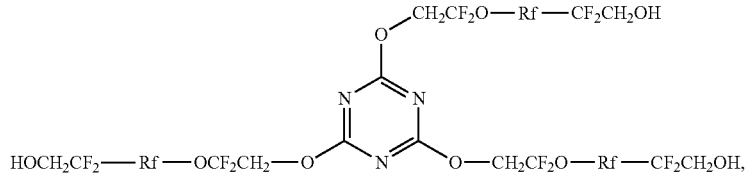

wherein $R_f$ is $(CF_2CF_2O)_m(CF_2O)_n$, and m/n is about 1

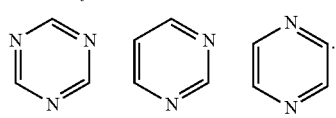

* * * * *